(12) United States Patent
Hofmann et al.

(10) Patent No.: US 8,425,489 B2
(45) Date of Patent: Apr. 23, 2013

(54) DRAINAGE TUBE DEVICE AND COUPLING UNIT

(75) Inventors: Adrian Hofmann, Lucerne (CH); Ignaz Henzen, Hünenberg (CH); Daniel Zanetti, Cham (CH)

(73) Assignee: Medela Holding AG, Baar (CH)

( * ) Notice: Subject to any disclaimer, the term of this patent is extended or adjusted under 35 U.S.C. 154(b) by 421 days.

(21) Appl. No.: 12/774,064

(22) Filed: May 5, 2010

(65) Prior Publication Data

US 2010/0286596 A1 Nov. 11, 2010

(30) Foreign Application Priority Data

May 8, 2009 (CH) .......................... 726/09

(51) Int. Cl.
*A61M 27/00* (2006.01)
(52) U.S. Cl.
USPC .......................... 604/540; 604/541
(58) Field of Classification Search .................. 604/317; 403/309
See application file for complete search history.

(56) References Cited

U.S. PATENT DOCUMENTS

| | | | |
|---|---|---|---|
| 3,851,650 A | 12/1974 | Darling | |
| 4,509,554 A | 4/1985 | Failla | |
| 4,541,457 A | 9/1985 | Blenkush | |
| 5,331,689 A * | 7/1994 | Haq | 4/144.1 |
| 8,002,758 B2 * | 8/2011 | Kamen et al. | 604/320 |
| 2005/0256461 A1 * | 11/2005 | DiFiore et al. | 604/247 |
| 2007/0156104 A1 * | 7/2007 | Lockwood et al. | 604/305 |
| 2009/0281526 A1 * | 11/2009 | Kenny et al. | 604/543 |
| 2011/0301557 A1 * | 12/2011 | Singh et al. | 604/319 |

FOREIGN PATENT DOCUMENTS

| | | |
|---|---|---|
| EP | 0599472 | 6/1994 |
| EP | 0795342 | 9/1997 |
| EP | 1600676 | 11/2005 |
| EP | 1840443 | 10/2007 |
| EP | 1920791 | 5/2008 |
| WO | 94/20152 | 9/1994 |
| WO | 97/28840 | 8/1997 |

(Continued)

OTHER PUBLICATIONS

International Search Report for corresponding PCT App. No. PCT/CH2010/000114 Dated Aug. 18, 2010.

*Primary Examiner* — Susan Su
(74) *Attorney, Agent, or Firm* — McDonnell Boehnen Hulbert & Berghoff LLP (57) ABSTRACT

A drainage tube device for removing fluids by suction from a human or animal body comprises a coupling unit with first and second coupling parts that can be connected to each other in a leaktight manner, a first valve that is arranged in the first coupling part, and a drainage tube with an end that is directed towards the patient and is held in the second coupling part. The drainage tube has a multi-lumen design with a drainage conduit and at least one auxiliary conduit. This drainage conduit and at least one of said auxiliary conduits are in fluidic communication with each other at their end directed towards the patient and arranged inside the second coupling part. The drainage tube device further comprises a second valve, which is arranged in the second coupling part and which opens and closes the drainage conduit. The drainage tube device and the coupling unit according to the invention are of simple construction but nonetheless permit many functions. In particular, they prevent dripping when the connection is released, and they allow pressure to be measured near the patient.

17 Claims, 10 Drawing Sheets

FOREIGN PATENT DOCUMENTS

| | | |
|---|---|---|
| WO | 01/34223 | 5/2001 |
| WO | 2006/020228 | 2/2006 |
| WO | 2007/014281 | 2/2007 |

* cited by examiner

DRAINAGE TUBE DEVICE AND COUPLING UNIT

CROSS REFERENCE TO RELATED APPLICATIONS

The present applications claims priority to Swiss Patent Application No. 0726/09, filed May 8, 2009, the entire contents of which are incorporated herein by reference.

TECHNICAL FIELD

The present invention relates to a drainage tube device, and more particularly to a coupling unit for use with such a drainage tube device.

PRIOR ART AND BACKGROUND OF THE INVENTION

Drainage systems for removing body fluids by suction, for example for thorax drainage, for liposuction, for aspiration of blood or secretions during operations and for wound drainage, are known.

For this purpose, for example, a catheter is guided into a body cavity or a suction head is guided onto a wound. The catheter or the suction head is connected to a suction conduit that leads into a secretion collection container. A central vacuum system or a suction pump is used to generate an underpressure (relative negative pressure) in the suction conduit, such that the body fluid is sucked through the suction conduit into the collection container. In addition to the suction conduit, it is also known to use a service conduit which, for example, permits evacuation of air from the suction conduit.

Thus, WO 94/20152 discloses a drainage device for removing fluids by suction from a body cavity, in particular the pleural cavity. The device has a drainage conduit for removing the fluids by suction, and a vacuum pump for generating an underpressure in the body cavity. A gas can be introduced into the body cavity via an auxiliary conduit. This auxiliary conduit, at the end directed towards the patient, is in fluidic communication with the drainage conduit. Auxiliary conduit and drainage conduit are preferably arranged in a double-lumen tube. A pressure gauge is arranged at the end of the auxiliary conduit directed away from the patient, and it is proposed that the pressure difference between the flows in the auxiliary conduit and drainage conduit be determined.

U.S. Pat. No. 3,851,650 discloses a drainage tube with a connector piece for connection to a catheter. The drainage tube has a double-lumen design with a drainage conduit for removal of body fluid from a patient by suction and an auxiliary conduit for supply of air. To ensure that the body fluid removed by suction does not pass into the auxiliary conduit, a valve which is capable of opening the drainage conduit in one direction and sealing it in an opposite direction is arranged at the end of the auxiliary conduit directed towards the patient.

EP 0 599 472 likewise discloses the use of a double-lumen tube in a medico-surgical suction system.

These tubes require coupling units, for example in order to connect them to the suction catheter or to a suction head for a wound dressing or in order to increase the total length of the drainage tube. To ensure that no bodily secretions escape during release of the coupling unit, the drainage tube is usually first of all closed by a clamp. However, this makes handling more difficult and takes up more time when changing the drainage device. It is also sometimes forgotten to close the clamp. Moreover, at the time of reconnection, it is sometimes forgotten to open the clamp again, with the result that the drainage is not continued. Even when a monitoring system is present, it still takes some time before an error is reported. In addition, the coupling unit must not impede the supply of air to the suction conduit by way of an auxiliary conduit and/or a pressure measurement in the suction conduit.

In other fields at least, coupling units are known which have integrated valves and which thus prevent dripping from an uncoupled tube.

Thus, WO 2007/014281 and EP 1 840 443 describe coupling units for leaktight connection of two tubes, with a valve being arranged in each part of the coupling unit.

U.S. Pat. No. 4,541,457 discloses a coupling unit for a $CO_2$ conduit. The unit comprises a male coupling part and a female coupling part. A valve which allows or prevents a flow stream in two opposite directions is arranged in the female coupling part, while a nonreturn valve is arranged in the male coupling part.

U.S. Pat. No. 4,509,554 discloses a coupling unit for high-pressure and low-pressure uses, with a male coupling part and a female coupling part. Both coupling parts are each equipped with an inner spring-biased valve and an outer spring-biased valve.

SUMMARY DISCLOSURE OF THE INVENTION

It is therefore an object of the invention to create an improved drainage tube device, and in particular a drainage tube device having a coupling unit, which in particular permit a pressure measurement.

This object is achieved in one embodiment by a drainage tube device and a coupling unit according to the invention for removing fluids by suction from a human or animal body comprises:

a coupling unit with first and second coupling parts that can be connected to each other in a leaktight manner, a first valve that is arranged in the first coupling part, and a drainage tube with an end that is directed towards the patient, i.e., an end at the patient side, which is held in the second coupling part.

The drainage tube in this embodiment has a multi-lumen design and a drainage conduit and at least one auxiliary conduit. This drainage conduit and at least one of said auxiliary conduits are in fluidic communication with each other at their end directed towards the patient and arranged inside the second coupling part. The drainage tube device further comprises a second valve, which is arranged in the second coupling part and which opens and closes the drainage conduit.

The coupling unit according to the invention for use in a drainage tube device preferably comprises first and second coupling parts that can be connected to each other in a leaktight manner. It also has a first valve that is arranged in the first coupling part. The second coupling part has a recess for securing an end of a multi-lumen drainage tube directed towards the patient. The drainage tube preferably has a drainage conduit and at least one auxiliary conduit, wherein the recess permits fluidic communication between this drainage conduit and at least one of said auxiliary conduits at their end directed towards the patient, and arranged inside the second coupling part. The coupling unit of this embodiment further comprises a second valve, which is arranged in the second coupling part and which opens and closes the drainage conduit.

The foregoing drainage tube device and this coupling unit permit simple connection and separation of the drainage tube to and from other components, in particular another drainage tube, a catheter or a suction head, without clamping being needed. Dripping is avoided by virtue of the valves.

The first valve is preferably always closed in the separated state of the coupling parts, and the second valve is preferably always closed in the absence of an underpressure in the drainage conduit.

If the two coupling parts are connected releasably to each other via a snap-fit connection, this ensures simple connection and separation of the two parts. The two coupling parts can be connected to each other directly. However, they can also be connected to each other indirectly via a bridging part. This bridging part preferably has a first end component and a second end component, wherein the first end component can be connected to the first coupling part and the second end component to the second coupling part in a leaktight manner. The first end component is preferably designed the same as the second coupling part, and the second end component is preferably designed the same as the first coupling part. However, the bridging part preferably does not have any valves itself.

The use of a multi-lumen tube stiffens the drainage conduit and prevents kinking of the conduit. It is advantageous to use several, most preferably exactly three, auxiliary conduits, which are distributed peripherally and in a uniform manner about the centrally arranged drainage conduit.

A hollow space is preferably present in the second coupling part, at that end of the drainage tube directed towards the patient, which hollow space permits the communicating connection between the drainage conduit and the at least one auxiliary conduit. This hollow space permits a pressure measurement, in particular a measurement of the pressure difference between the at least one auxiliary conduit and the drainage conduit. Pressure measurement is therefore possible near the patient, without sensors having to be mounted in the coupling part.

The first valve is preferably a valve which allows or prevents a flow stream in two opposite directions. In a preferred embodiment, the first valve has an elastically deformable piston which is held in the first coupling part and whose deformation takes place upon connection of the first coupling part to the second coupling part or, if it is present, to the bridging part. However, other types of such valves can also be used, for example spring-biased valves.

The second valve can be a one-way valve or a valve which allows or prevents a flow stream in the two opposite directions. It preferably closes only the drainage conduit, not the auxiliary conduit. It is preferably arranged in such a way that, in the closed state of the second valve, there is no communicating connection between the drainage conduit and the at least one auxiliary conduit at that end of the tube directed towards the patient, i.e., the end directed towards the coupling part.

If the second valve is designed as a duckbill valve, it takes up relatively little space, and the coupling unit can be produced relatively inexpensively. A very simple and inexpensive structure is permitted if the second valve is fitted onto that end of the drainage tube directed towards the patient or protrudes at least partially into the drainage conduit. In this way, it can be inserted together with the drainage tube into the coupling part.

The drainage tube is usually adhesively bonded into the coupling part or welded to it. The second valve is preferably held in an interference fit between an abutment of the second coupling part and that end of the drainage tube directed towards the patient.

The coupling unit according to the invention advantageously has a small number of component parts and is therefore simple and inexpensive to produce. It further ensures a relatively high degree of functionality during use.

Other advantageous features are further described in the following detailed description of the invention.

BRIEF DESCRIPTION OF THE FIGURES

A preferred embodiment of the invention is described below with reference to the drawings. These serve only for illustrative purposes and are not intended to be limiting. In these drawings.

DETAILED DESCRIPTION

Figure 1:
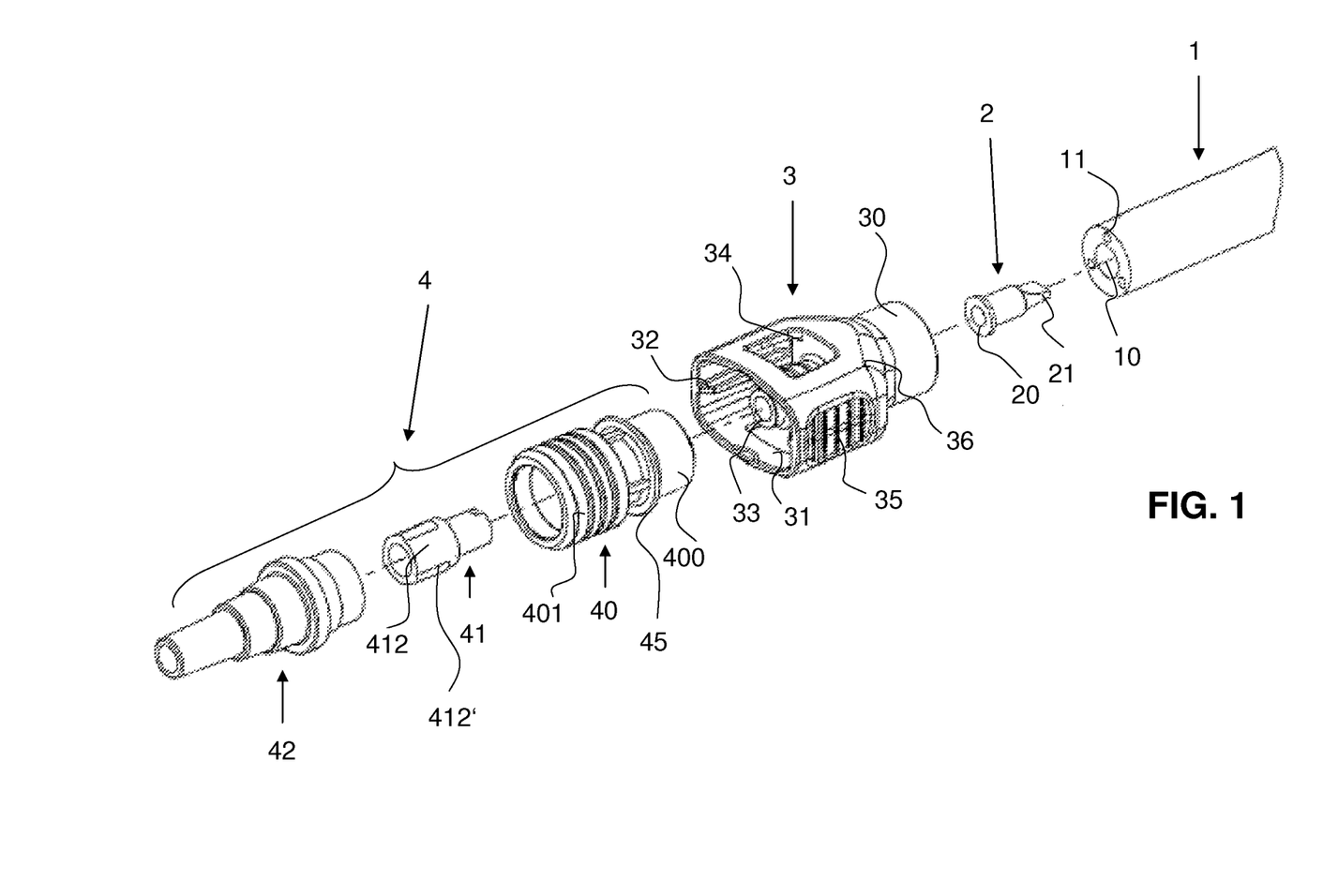
FIG. 1 shows an exploded view of the drainage tube device according to the invention.
Figure 2:
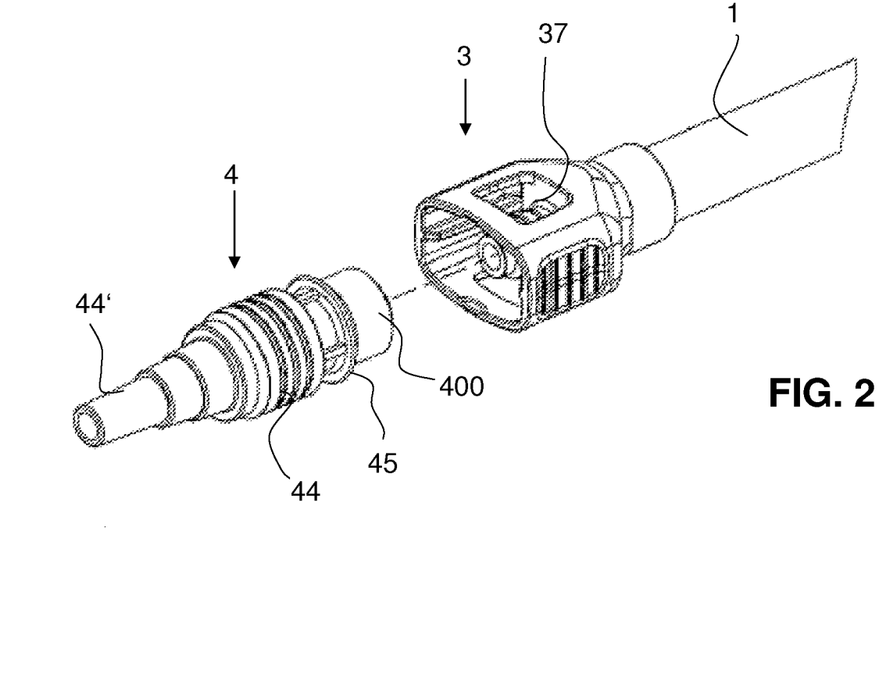
FIG. 2 shows the drainage tube device according to FIG. 1, with the coupling unit uncoupled.

A drainage tube device according to the invention is shown in FIGS. 1 and 2. It has a first coupling part 4 with a first valve 41, a drainage tube 1, a second valve 2, and a second coupling part 3.

The drainage tube 1 is a multi-lumen tube, preferably made of PVC. It comprises at least two conduits, namely a drainage conduit 10 and an auxiliary conduit 11. The drainage conduit 10 preferably extends centrally and the auxiliary conduit in the peripheral area. The diameter of the auxiliary conduit 11 is preferably a multiple smaller than that of the drainage conduit 10. The auxiliary conduit 11 and the drainage conduit 10 preferably extend completely separate from each other and have no connection to each other.

In the embodiment shown, three auxiliary conduits 11 are present, which are arranged in a uniform manner about the circumference and distributed about the drainage conduit. The three auxiliary conduits 11 preferably all have the same cross-sectional area. However, they can also have different sizes of lumen.

This drainage tube 1 can be produced in a known manner, for example by extrusion.

The second valve 2 shown here is a one-way valve. However the valve can also be a valve which closes or opens the flow stream in the two opposite directions. Here, a duckbill valve is used. It is preferably made of silicone. It has a peripheral, radially projecting and plane flange 20, and a beak 21 which opens when there is a corresponding external pressure on one side and closes in the absence of this pressure. The beak 21 is directed towards the drainage conduit 10.

The drainage tube 1 is connected releasably, preferably fixedly, to the second coupling part 3. Its end directed towards the patient is preferably welded into this coupling part 3 or adhesively bonded to it. The second end (not shown) of the drainage tube 1 leads to a suction unit, for example a vacuum pump or a central vacuum.

The second coupling part 3 and the first coupling part 4 are preferably made of plastic. The second coupling part 3 is preferably made of PVC or ABS. The first coupling part 4 is preferably made of hard PVC, PC or ABS. They are preferably designed in one piece.

The second coupling part 3 has a hollow cylindrical connector stub 30 for receiving the valve 2 and the drainage tube 1. The connector stub 30 preferably has a round cross section. A hollow main body 36 is formed integrally onto this connector stub 30 and preferably has an approximately rectangular cross section with convexly curved broad sides. At its two narrow sides lying opposite each other, it has in each case a pressure area that can be pressed in slightly by hand in order to deform the shape of the main body 36. The deformability is facilitated by two windows 34 arranged in the broad sides of the main body 36. In this way, the first coupling part 4 described below can be easily uncoupled from the second coupling part 3. Side ribs 32, which are arranged on the narrow sides and project inwards into the main body 36, serve as limit stops when the main body 36 is pressed together.

The main body 36 encloses an insertion opening 31 in which a plug element 33, spaced apart from the side walls of the main body 36, projects into the latter and forms the mating piece for the connector stub 30. The first coupling part 4 can be fitted into this insertion opening 31 and engages around the plug element 33. Ribs 37 or sealing beads may be present. These are arranged on the plug element 33 and extend around the outer circumference of said plug element 33 and they hold the first coupling part 4 in a releasable connection to the second coupling part 3.

The first coupling part 4 can be designed in one piece or several pieces. In the case where it is composed of several pieces, however, the individual parts are preferably connected fixedly to one another in such a way that they cannot be disconnected without being destroyed. They are preferably adhesively bonded or welded to one another or are connected to one another by means of retainer ribs such that separation is difficult.

The first coupling part 4 has a hollow cylindrical main body 40 which has a hollow cylindrical connector stub 400 directed towards the second coupling part 3. This connector stub 400 can be pushed over the plug element 33. A flange 45, which projects radially from this stub 400 and extends between main body 40 and stub 400, engages behind the window 34 in the assembled state and thus serves as a snap-fit element of the snap-fit connection between the two coupling parts 3, 4. This can be seen in FIG. 5.

As can further be seen in FIGS. 1 and 2, a first valve 41 is arranged in the first coupling part 4. This first valve 41 is described in detail below. The first coupling part 4 further comprises a tube attachment piece 42 for attaching the drainage tube device to a suitable connecting element for the desired drainage application. This can be a catheter, another tube, a suction body or another suitable connecting element.

The tube attachment piece 42 preferably has a structure tapering towards its free end, in order to make attachment easier. On its outer circumference, the structure can be provided with ribs, steps 44', a Christmas tree configuration or other suitable means. The attachment piece 42 or, as is shown here, the main body 40 preferably has an outer thread 44 in order to offer a further attachment possibility.

Figure 3:
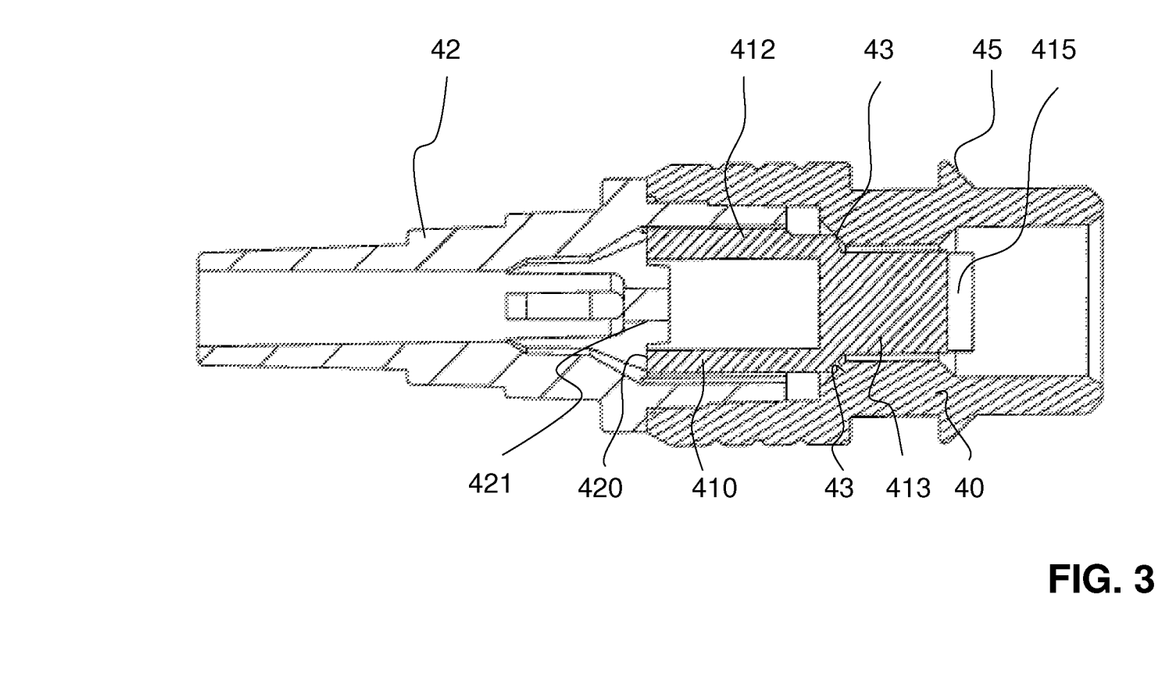
FIG. 3 shows a longitudinal section through a first coupling part of the coupling unit according to FIG. 2.

It will be seen from FIG. 3 how the first valve 41 is held between main body 40 and tube attachment piece 42. The first valve 41 has a first hollow cylindrical valve body 410 and, formed integrally thereon, a second valve body 413. The second valve body 413 is likewise a circular cylinder. However, it is solid, i.e., filled. Ribs 412 and indents 412' are preferably present on the outer circumference of the first valve body 410, as can be seen in FIGS. 1 and 3. The second valve body 413 is flat at its free end, where a slit 415 extends in this plane and preferably runs diametrically across the full width of the valve body. This first valve is preferably made of silicone.

At its end directed towards the main body 40, the tube attachment piece 42 has a supporting structure 421, which forms a peripheral projection 420. The second valve 41 lies with a flat end of its first valve body 410 on this projection 420 or abuts against this limit stop 420.

As can be seen from FIG. 3, the first valve 41 seals the through-channel in the first coupling part 4 in a leaktight manner. The peripheral sealing area is designated by reference sign 43 in FIG. 3.

As is shown in FIG. 2, this assembled first coupling part 4 can now be connected in a releasable plug-type connection to the second coupling part 3 and to the drainage tube 1 connected to the latter.

Figure 4:
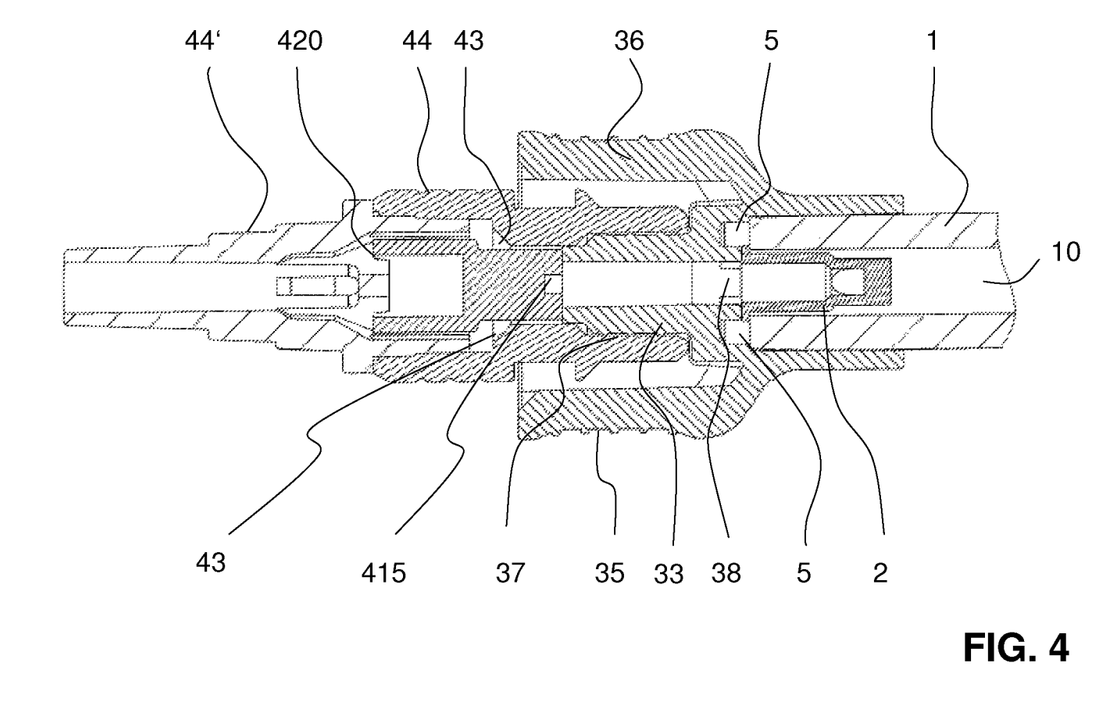
FIG. 4 shows a longitudinal section through a drainage tube device according to FIG. 1, in the assembled state of the coupling unit.
Figure 5:
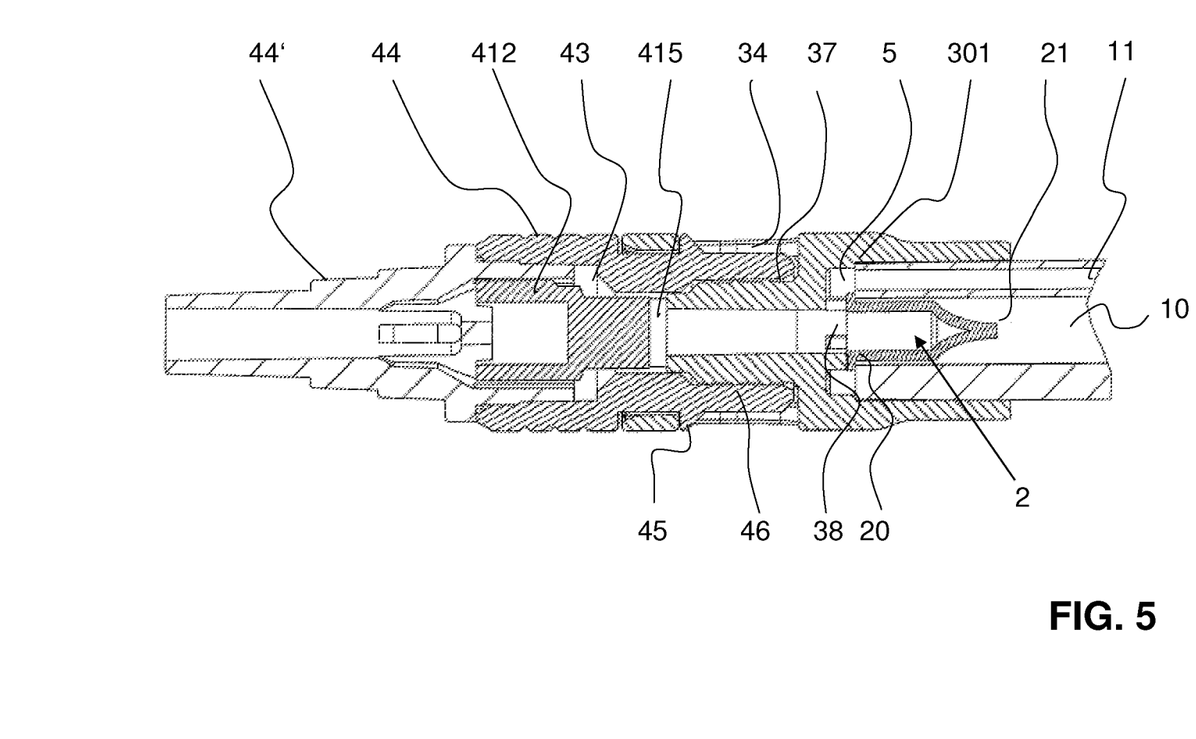
FIG. 5 shows a longitudinal section through the drainage tube device according to FIG. 4, in a plane perpendicular to this Figure.

This assembled state is shown in FIGS. 4 and 5. These figures also show how the drainage tube 1 is connected to the second coupling part 3. This is now explained first.

In the inside of the connector stub, the second coupling part 3 has a peripheral projection 301 that serves as an abutment for the flat end of the drainage tube 1. The shoulder has such a narrow configuration that not only the drainage conduit 10 but also the auxiliary conduits 11 open into this common hollow space 5. The drainage tube 1 is preferably welded to the connector stub in this position or adhesively bonded to it.

The second valve 2 is fitted with its beak 21 into the drainage conduit 10 such that it opens towards the drainage conduit 10. It lies with its flange 20 on the flat end of the drainage tube 1. In doing so, it does not cover the apertures of the auxiliary conduits 11. On its opposite side, the flange 20 bears on a crown, a slotted ring or a grate 38 of the second coupling part 3, such that it is held in the interference fit between drainage tube 1 and this grate 38. The grate 38 is located in the hollow space 5, in which it does not impede fluid communication between the auxiliary conduits 11 and the drainage conduit 10.

As will now be seen from FIGS. 4 and 5, the plug element 33 is inserted into the recess of the connector stub 400. In the assembled state of the coupling unit, it pushes in the direction of the projection 420 of the first coupling part 4. In this way, the first valve 41, in particular the first valve body 410, is compressed and deformed. The sealing area 43 is freed and, by virtue of the slit 415, a continuous channel is created between the free end of the first coupling part 4 and the free end of the second coupling part 3 or the drainage tube 1. This channel can best be seen in FIG. 5.

The first valve 41 thus acts as a valve which opens and closes in both directions as long as the two coupling parts 3, 4 are connected to each other. As soon as the second coupling part 3 is removed again, the elastically configured second valve 41 recovers its original shape and closes the sealing area 43. The first coupling part 4 is therefore open only in the assembled state of the coupling unit.

Instead of the elastically deformable first valve 41, it is also possible to use another automatically closing valve, for example a spring-loaded valve. This is shown schematically in FIGS. 6 to 12.

The second valve 2 is always closed in the absence of an underpressure in the drainage conduit 10.

The coupling between the two coupling parts 3, 4 is released by applying pressure to the lateral pressure areas 35 until the flange 45 of the first coupling part 4 is freed from the main body 36 of the second coupling part 3. In this way, a quick-coupling mechanism is formed that is easy to operate but nonetheless reliable and leaktight.

Figure 6:
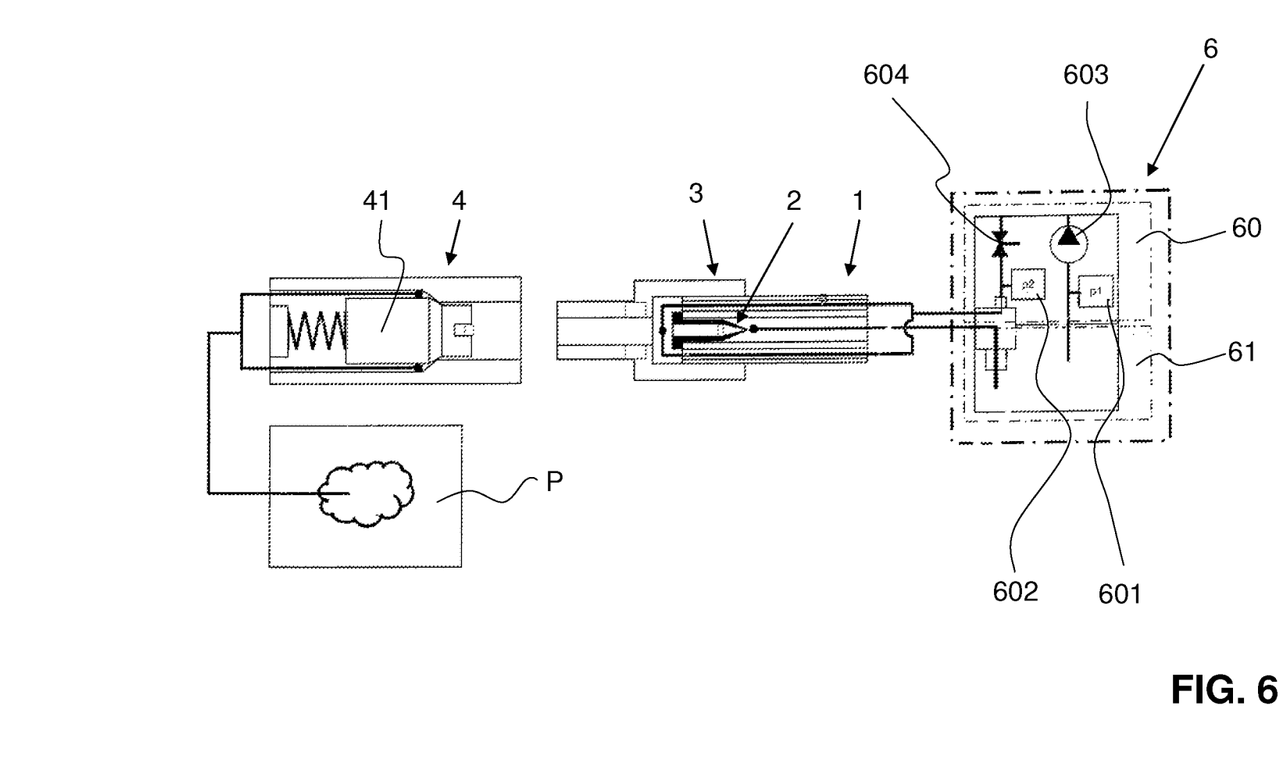
FIG. 6 shows a schematic representation of the drainage tube device according to the invention with a drainage unit.
Figure 7:
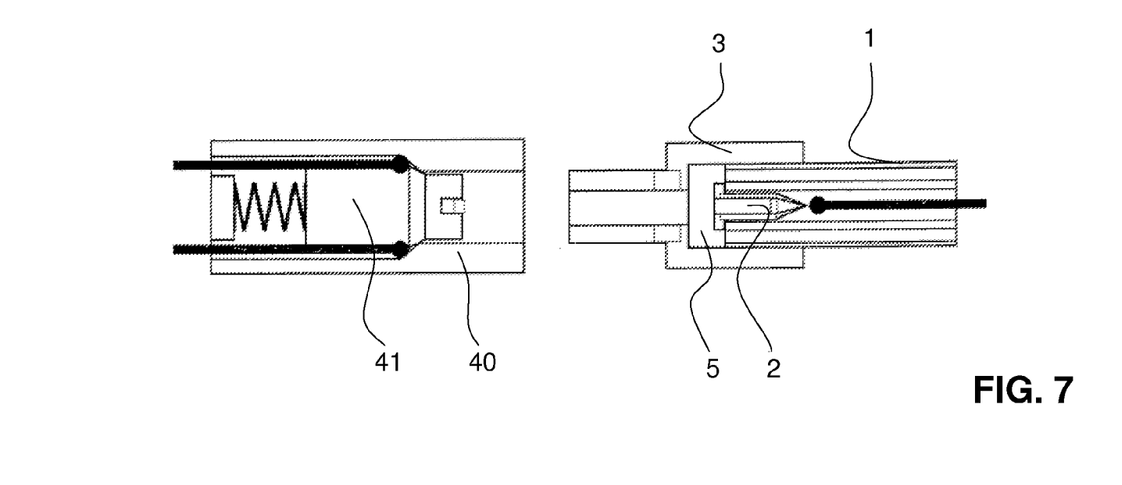
FIG. 7 shows a schematic representation of the coupling unit according to the invention in the uncoupled state.

FIG. 6 shows the drainage tube device in a drainage application. P designates the patient. The drainage tube 1, more precisely the drainage conduit 10, is connected to a drainage unit 6 and leads into a drainage container 61. A conduit leads from the drainage container 61 to a pump assembly 603 of a vacuum pump 60. The auxiliary conduit 11 also leads into the drainage unit, where it opens into the vacuum pump 60.

A nonreturn valve 604 arranged in the suction pump permits a flushing operation when it is in its open position. That is to say, air can be supplied to the hollow space 5 via the auxiliary conduit 11, and the drainage conduit 10 can be flushed with air.

At least one pressure sensor is present in the suction pump 60, or in the area between suction pump and drainage tube 1, in order to determine the pressure in the hollow space 5. Two pressure sensors 601, 602 are present here, such that a pressure difference between drainage conduit 10 and auxiliary conduit 11 can be measured. Known and commercially available sensors can be used as pressure sensors.

The auxiliary conduits 11 therefore serve, on the one hand, for measuring the pressure in the hollow space or the difference in pressure with respect to the drainage conduit 10 and, on the other hand, for evacuating and flushing the drainage conduit 10.

In FIG. 6, thick lines indicate the communicating connection in the individual channels and conduits. Within the drainage conduit 10, this thick line ends at a point. This is intended to illustrate that the second valve 2 is closed and therefore this drainage conduit 10 is closed at this end. The same applies to the channel in the first coupling part 4. Here, the first valve 41 is closed, such that here too there is no continuous channel present. The same situation is shown again in FIG. 7.

Figure 8:
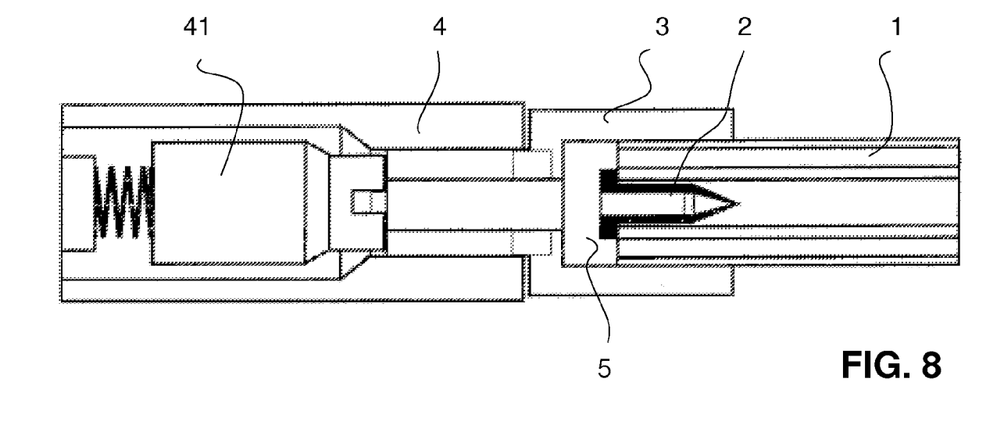
FIG. 8 shows the coupling unit according to FIG. 7 in the assembled state.

In FIG. 8, the coupling parts 3, 4 are connected to each other, and the first valve 41 frees the channel. The second valve 2 is still closed, however.

Figure 9:
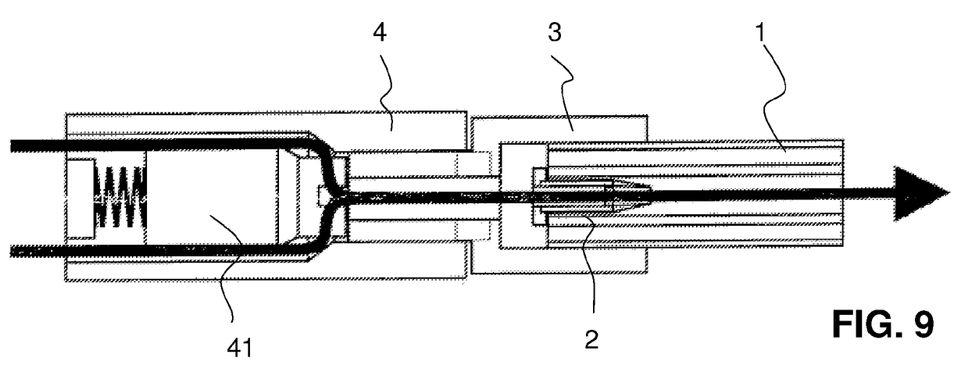
FIG. 9 shows the coupling unit according to FIG. 7 in drainage mode, with a constant underpressure.

In FIG. 9, the thick arrow indicates the flow of the body fluid removed by suction. This is a drainage mode with constant application of underpressure. Not only is the first valve 41 opened now, but also the second valve 2, and the channel extends continuously through the coupling unit from the patient to the secretion collection container 61.

Figure 10:
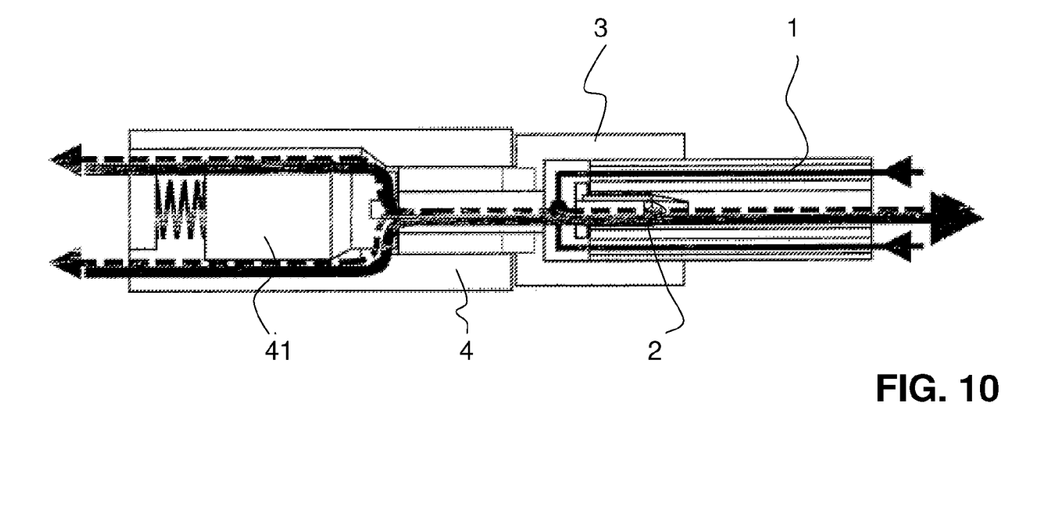
FIG. 10 shows the coupling unit according to FIG. 7 in drainage mode, with intermittent underpressure.

FIG. 10 shows an operating mode with intermittent application of a vacuum or underpressure. The sequences can, for example, comprise a suction phase of about 6 minutes and a break interval, under atmospheric pressure, of about 3 minutes. During the break interval, not only is air evacuated via the auxiliary conduits 11, but flushing of the drainage conduit 10 preferably thereby also takes place. The second valve 2 is open.

Figure 11:
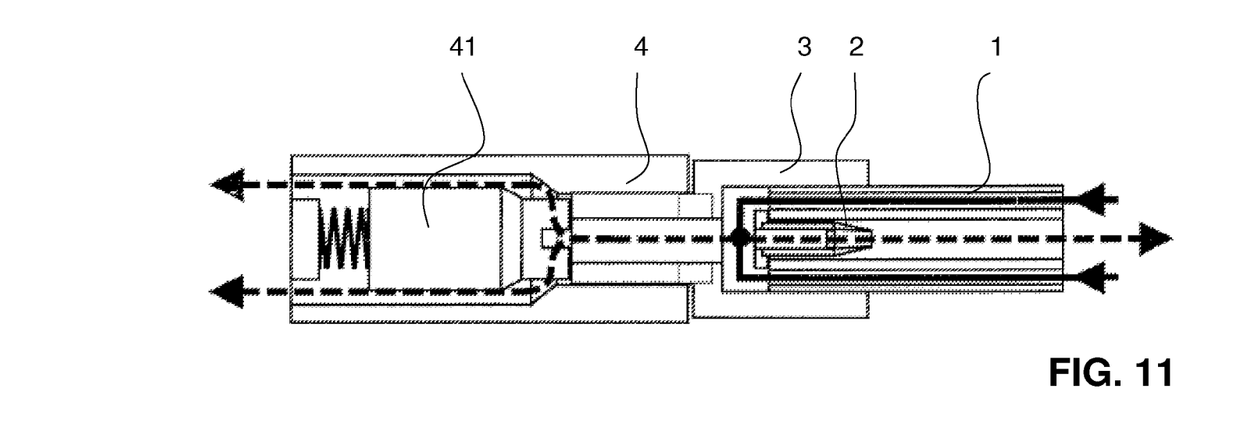
FIG. 11 shows the coupling unit according to FIG. 7 during flushing of the conduit.

FIG. 11 shows a flushing operation with constantly applied underpressure. The second valve 2 is open, and the vacuum on the patient side, that is to say at the free end of the first coupling part 4, is reduced, as in the operation in FIG. 10.

Figure 12:
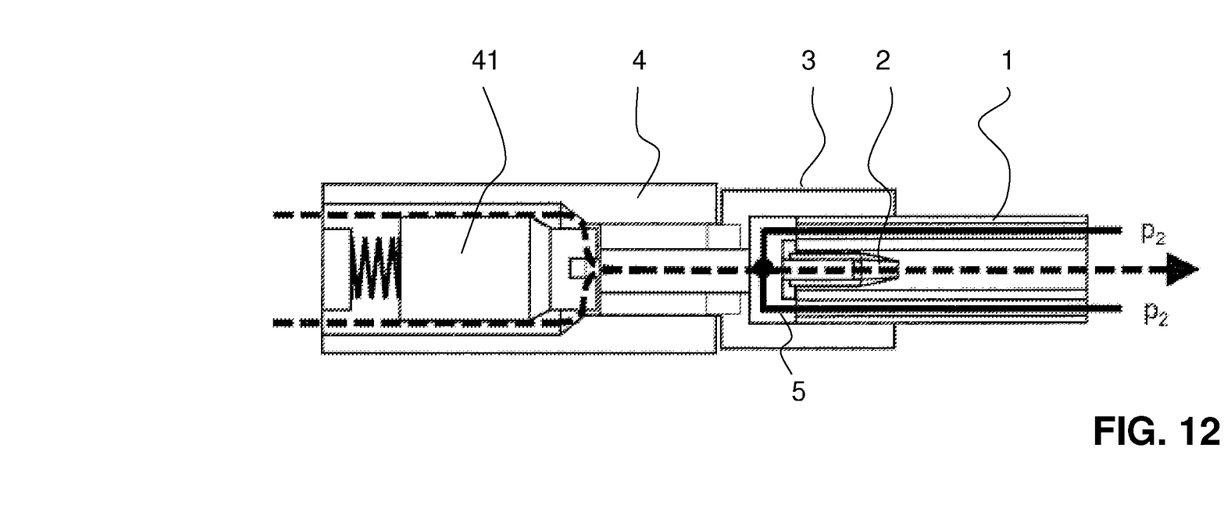
FIG. 12 shows the coupling unit according to FIG. 7 during pressure measurement.

FIG. 12 now shows a pressure measurement. This is possible in the operation according to all of FIGS. 9 to 11.

Figure 13:
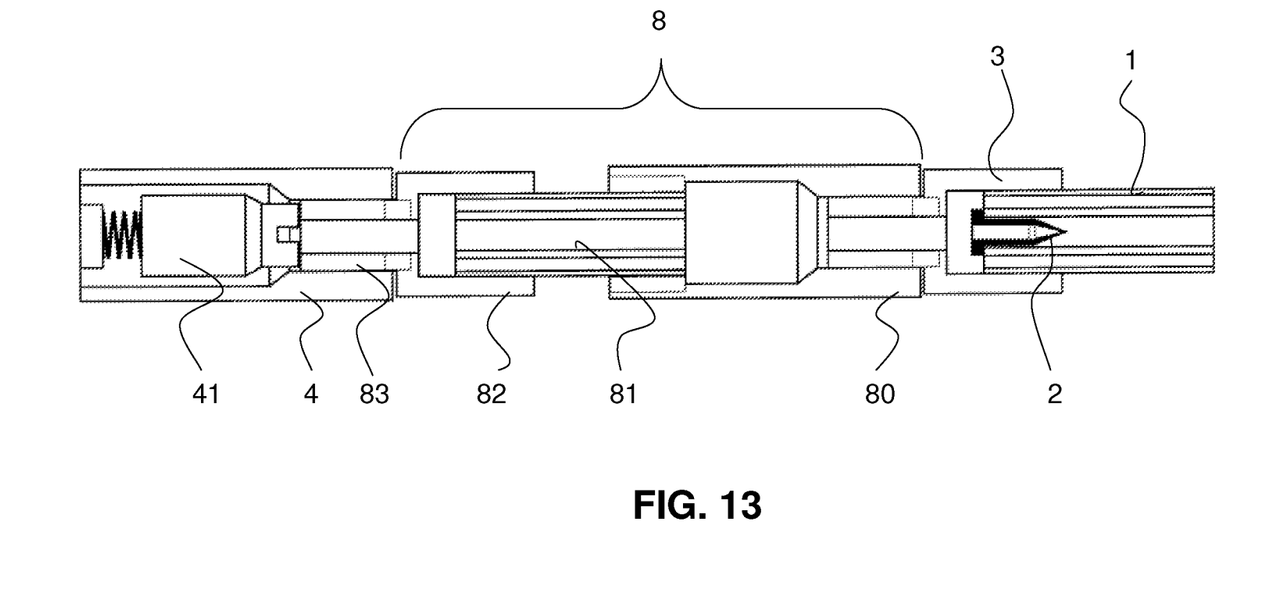
FIG. 13 shows a coupling unit according to the invention with a bridging part.

FIG. 13 shows an embodiment in which the first and second coupling parts 3, 4 are not connected directly to each other. The two coupling parts 3, 4 are here designed in the same way as in the example described above. That is to say, they can also be plugged directly into each other.

In FIG. 13, a bridging part 8 is present with a first end and a second end, wherein the first end can be connected to the first coupling part 4 and the second end can be connected to the second coupling part 3. The first end for this purpose has a main body 82 which is preferably designed the same as the above-described main body 36 of the second coupling part 3. It is designed at least with the same function. A plug element 83 is again integrally formed in the main body 36 and is preferably designed the same as the plug element 33 of the above-described second coupling part 3.

The second end forms the exact match, or at least a functional match, of the corresponding part of the first coupling part 4. It has a connector stub 80, which corresponds to the connector stub 400 of the first coupling part 4.

The middle area 81 between these two ends of the bridging part 8 can be of any desired configuration.

The drainage tube device according to the invention and the coupling unit according to the invention are of simple construction but nonetheless permit many functions. In particular, they prevent dripping when the connection is released, and they allow pressure to be measured near the patient.

Various exemplary embodiments and methods have been described above. Those skilled in the art will understand, however, that changes and modifications may be made to those examples without departing from the scope and spirit of the present invention. It should be further noted that the above overview is meant to be illustrative, not limiting. That is, additional and/or different features may be present in some embodiments of the present invention.

What is claimed is:

1. A drainage tube device for removing fluids by suction from a human or animal body, comprising
    a coupling unit with first and second coupling parts that can be connected to each other in a leaktight manner,
    a first valve that is arranged in the first coupling part, and
    a drainage tube with an end that is directed towards the patient, which is held in the second coupling part,
    wherein the drainage tube has a multi-lumen design with a drainage conduit and at least one auxiliary conduit,
    the drainage conduit and at least one of said auxiliary conduits, when arranged inside the second coupling part, are in fluidic communication with each other at ends directed towards the patient, and
    a second valve, which is arranged in the second coupling part and which opens and closes the drainage conduit.

2. The drainage tube device according to claim 1, wherein the first valve is a valve which enables or prevents a flow stream in two opposite directions.

3. The drainage tube device according to claim 1 further comprising a hollow space present in the second coupling part at the end of the drainage tube directed towards the patient, wherein the hollow space creates a communicating connection between the drainage conduit and the at least one auxiliary conduit and permits a pressure measurement.

4. The drainage tube device according to claim 3 wherein the coupling unit is designed without sensors.

5. The drainage tube device according to claim 3 wherein the pressure measurement is a measurement of the pressure difference between the at least one auxiliary conduit and the drainage conduit.

6. The drainage tube device according to claim 1 wherein the second valve is fitted onto the end of the drainage tube directed towards the patient.

7. The drainage tube device according to claim 1 wherein the second valve is fitted into the drainage conduit.

8. The drainage tube device according to claim 7 wherein the second valve is held in an interference fit between an abutment of the second coupling part and the end of the drainage tube directed towards the patient.

9. The drainage tube device according to claim 1 wherein the second valve is a one-way valve.

10. The drainage tube device according to claim 9 wherein the one-way valve is a duckbill valve.

11. The drainage tube device according to claim 1 wherein the two coupling parts can be connected to each other releasably.

12. The drainage tube device according to claim 11 wherein the two coupling parts can be connected to each other via a snap-fit connection.

13. The drainage tube device according to claim 1 wherein a bridging part with a first end component and a second end component is present, and wherein the first end component can be connected to the first coupling part and the second end component to the second coupling part in a leaktight manner.

14. The drainage tube device according to claim 13 wherein the first valve has a deformable piston which is held in the first coupling part and whose deformation takes place upon connection of the first coupling part to the second coupling part or, if it is present, to the bridging part.

15. The drainage tube device according to claim 1 wherein the drainage conduit is arranged generally centrally in the drainage tube, and the at least one auxiliary conduit is located peripherally relative to the drainage tube.

16. The drainage tube device according to claim 15, wherein at least three auxiliary conduits are present and are distributed peripherally in a generally uniform manner about and spaced from the circumference of the drainage tube.

17. A coupling unit for use in a drainage tube device comprising:
   first and second coupling parts that can be connected to each other in a leaktight manner, and
   a first valve that is arranged in the first coupling part,
   the second coupling part has a recess for securing an end of a multi-lumen drainage tube directed towards the patient, the drainage tube having a drainage conduit and at least one auxiliary conduit, the recess permits fluidic communication between the drainage conduit and at least one of the auxiliary conduits at ends directed towards the patient when the drainage tube is arranged inside the second coupling part, and
   a second valve, which is arranged in the second coupling part and which opens and closes the drainage conduit.

* * * * *